United States Patent [19]

Bowald et al.

[11] Patent Number: 5,641,505

[45] Date of Patent: Jun. 24, 1997

[54] POROUS FLEXIBLE SHEET FOR TISSUE SEPARATION

[75] Inventors: Staffan Folke Bowald, Almunge; Gunilla Eva Johansson, Göteborg, both of Sweden

[73] Assignee: Astra Tech Aktiebolag, Sodertalje, Sweden

[21] Appl. No.: 357,553

[22] Filed: Dec. 16, 1994

Related U.S. Application Data

[63] Continuation of Ser. No. 933,876, Aug. 21, 1991, abandoned, which is a continuation of Ser. No. 465,117, Apr. 25, 1990, abandoned.

[30] Foreign Application Priority Data

Jun. 27, 1988 [SE] Sweden ................... 8802414

[51] Int. Cl.$^6$ ........................ A61F 13/00
[52] U.S. Cl. .............. 424/443; 424/444; 424/422; 424/423; 424/426
[58] Field of Search ................... 424/443, 422, 424/423, 426, 444

[56] References Cited

U.S. PATENT DOCUMENTS

| | | | |
|---|---|---|---|
| 3,463,858 | 8/1969 | Anderson | 514/6 |
| 3,636,956 | 1/1972 | Schneider | 528/354 |
| 3,739,773 | 6/1973 | Schmitt | 128/92 BC |
| 3,982,543 | 9/1976 | Schmitt | 128/335.5 |
| 4,173,689 | 11/1979 | Lyman et al. | 521/64 |
| 4,355,426 | 10/1982 | MacGregor | 3/1.4 |
| 4,576,608 | 3/1986 | Homsy | 623/11 |
| 4,603,070 | 7/1986 | Steel | 428/88 |
| 4,603,695 | 8/1986 | Ikada et al. | 604/358 |
| 4,702,917 | 10/1987 | Schindler | 424/422 |
| 4,719,246 | 1/1988 | Murdoch et al. | 521/134 |
| 4,731,088 | 3/1988 | Collier | 623/22 |

FOREIGN PATENT DOCUMENTS

| | | |
|---|---|---|
| 0128501 | 12/1984 | European Pat. Off. . |
| 0130401 | 1/1985 | European Pat. Off. . |
| 0157178 | 10/1985 | European Pat. Off. . |
| 0217115 | 4/1987 | European Pat. Off. . |
| 2060524 | 6/1970 | France . |
| 8602843 | 10/1985 | WIPO . |

OTHER PUBLICATIONS

Bowald, Busch & Eriksson; Arterial Grafting with Polyglactin Mesh in Pigs; Jan 21, 1978, The Lancet p. 153.
Malm, Bowald, Bylock, Saldeen & Busch; Regeneration of Pericardial Tissue; Scand. J. Thor. Cardio. Surg. 26:15–21, 1992.
Malm, Bowald, Karacagil, Bylock & Busch; A New Biodegradable Patch; Scand. J. Thor. Cardio Surg. 26:19–14, 1992.
Malm, Bowald, Bylock & Busch; Prevention of Postoperative Pericardial Adhesions; J. Thor. Cardio. Surg., vol. 104, No. 3, pp. 600–607, Sep. 1992.
Vert et al., "Bioresorbability and biocompatibility of aliphatic polyesters", Journal of Materials Science: Materials in Medicine, vol. 3, pp. 432–446 (1992).
Holmes, P.A., "Applications of PHB—A Microbially Produced Biodegradable Thermoplastic", Phys. Technol., vol. 16, pp. 32–36 (1985).
Miller et al., "On the biodegradation of poly–β–hydroxybutyrate (PHB) homopolymer and poly–β–hydroxybutyrate–hydroxyvalerate copolymers", Biomaterials, vol. 8, Mar., pp. 129–137 (1987).
Malm et al., "1st World Congress of Pediataric Cardiac Surgery", Bergamo, Italy, Jun. 19–23 (1988).
Williams et al., "The Degradation of Polyhydroxybutyrate (PHB)" Biomaterial and Clinical Applications, edited by Pizzoferrato et al., pp.471–476 (1987).
Malm et al., "Tissue Regeneration after Reconstruction of the Pericardium with Synthetic Absorbable Patches", Prospectives in Pediatric Cardiology, vol. 2, Part 3, Jun., pp.282–283 (1990).

*Primary Examiner*—D. Gabrielle Phelan
*Attorney, Agent, or Firm*—White & Case

[57] ABSTRACT

A material for tissue separation at healing processes in injured soft tissue in mammals including man is described. The material consists of a porous flexible sheet of a protein-free bioresorbable polymer. Processes for preparation of the material and use thereof are also described.

20 Claims, No Drawings

POROUS FLEXIBLE SHEET FOR TISSUE SEPARATION

This application is a continuation of application Ser. No. 07/933,876, filed Aug. 21, 1992, now abandoned, which is a continuation of application Ser. No. 07/465,117, filed Apr. 25, 1990 (abandoned).

TECHNICAL FIELD

The present invention is related to a material for separation of injured tissue at healing processes. It is further related to a process for preparation of such material, and to use of the material in healing processes.

BACKGROUND OF THE INVENTION

In healing of injuries in soft tissue, scar tissue develops, which in many cases disturbs the function of the damaged organ and adjacent organs. This problem primarily occurs in healing of internal organs, while the problems in healing of skin and external mucosae may also be of cosmetic nature. Reference to injury and injured soft tissue herein primarily relates to incisions and other injuries caused by surgical operations in the organ subject to surgical correction, as well as in covering and adjacent organs. Among injuries caused by surgical operations is included injuries caused by surgical correction of congenital defects e.g. fistulas. The material according to the invention may also advantageously be employed in healing of injuries caused by external violence e.g. in accidents. A purpose with the invention is to facilitate and improve the healing by locking out undesired cells, other tissue and/or foreign particles. For this purpose, porous cloth of polytetrafluoroethylene such as Gore-Tex® is currently in use. The disadvantage with this is that foreign material will remain in the body, which may cause problems. Bowald et al. in The Lancet No. 8056, Jan. 21, 1978, page 153 describes the use of a knitted mesh of polyglactin 910 (Vicryl®) as an arterial substitute. A preclotted mesh was sutured as a patch graft or as an end to end tube in the thoratic aorta in pigs. This coarse-mesh material is only useful by deposition of fibrin intermingled with platelets and red blood cells in the mesh spaces. Further studies on coarse-mesh polyglactin material were reported in Surgery vol. 86, no 5, pp. 722–729, 1979, in Scand J Thor Cardiovasc Surg 15:91–94, 1981, in Muscle & Nerve 5:54–57, 1982 and in Acta Chir Scand 146:391–395, 1980. SE 8604571-3 describes the use of resorbable and non resorbable membranes for accelerating bone formation and bone healing. However, cellular processes of resorptive type are indicated as undesirable, as they may delay bone formation and damage the newly formed bone.

DESCRIPTION OF THE INVENTION

According to the invention it has now been made possible to avoid such problems as mentioned above in healing of soft tissue. The invention provides a material for tissue separation at healing processes in injured soft tissue in mammals including man, characterized in that it consists of a porous flexible sheet of a protein-free bioresorbable polymer having a pore size which permits passage of water and salts through the sheet but which locks out cells and other tissue particles. The material of the invention has been found to cause a specific stimulating effect on formation of macrophages in soft tissue. The macrophages release a growth factor which stimulates tissue healing. The material of the invention does not require preclotting or the presence of blood for functioning.

According to a preferred embodiment of the invention the material has a pore size up to 30 µm, preferentially 0.1–10 µm. The sheet thickness may be between 1 µm and 5 mm, but is preferably 10 µm to about 1 mm.

The material may according to the invention be prepared according to the following processes, of which non-woven technique, precipitation and laser technique are preferred:

Non-woven

Non-woven fibrous material is prepared as described in U.S. Pat. No. 4,603,070. Fibres are produced from a melt or solution of the polymer by pressing the material through a perforated outlet. The fibres are spread randomly, or with a main orientation, on a support (a still glass plate—a mobile net ribbon—other mould). In this manner a porous "cloth" is obtained which may be given varying porosity by modification of fibre dimension, spreading method, material thickness and/or by working up with heat/compression. The thickness of the cloth is preferably 300–500 µm.

Perforation

A homogenous film/cloth of the material may be perforated by e.g. laser technique to achieve porosity. In particular, a weak so called excimer laser may be employed together with a template of perforated stainless steel.

Precipitation (not applicable to PGA)

The polymer is dissolved in a solvent which may be selected from a first group comprising dimethyl formamide (DMF), dimethylacetamide (DMA), dimethyl sulphoxide (DMSO), and tetrahydrofuran (THF), or from a second group comprising chlorinated hydrocarbons such as chloroform and methylene chloride. Precipitation of the polymer may be achieved with a precipitation agent, which with the first group of solvents suitably is water, possibly with an addition of up to 20% solvent. With the second group of solvents ethanol and other lower alcohols may be used as a precipitation agent, possibly with an addition of up to 20% solvent. Both the solvent and the precipitation agent may be a mixture. Temperature and time at the precipitation may be selected to achieve any desired pore size.

Effervescence

By admixture of an effervescing agent which releases gas e.g. in contact with water (at precipitation) or on heating (in a melt).

Leaching

Soluble particles, for example salt, are suspended in a solution of the polymer/admixed into a melt thereof. After evaporation/solidification the particles are washed out of the material by leaching in a suitable solvent for the particles (but not for the polymer). This washing can be done completely, or partially provided that a non-toxic salt such as NaCl is employed, whereby the residual amount of salt may be allowed to leach out after implanting the material into the body.

The material is used according to the invention in healing of soft tissue, i.e. tissue that does not consist of cartilage, bone or teeth. Preferably the material is used for healing of injuries in the:

Circulatory system (heart, blood vessels such as the pulmonary artery)

Digestive organs (stomach, intestines, oral cavity, liver, pancreas)

Reproductive organs (uterus e.g. in a Caesarean section, ovaries, testes e.g. at undescended testis in boys, the Fallopian tubes, testicular ducts)

Urinary system (kidney, bladder, urethra)

Respiratory system (lungs, trachea, bronchi)

Other muscles (abdominal wall etc.)

Suitable bioresorbable materials for the purposes of the present invention may readily be chosen by one skilled in the art, e.g. among those that are either commercially available or have been described in literature or will be available in the future. As examples of such bioresorbable materials may be mentioned polymers based on polyglycolic acid (PGA), copolymers of glycolic acid and lactic acid, copolymers of lactic acid and ε-aminocapronic acid, and various lactide polymers. PGA esters are, e.g. described in U.S. Pat. No. 3 463 658, while copolymers of glycolic acid and lactic acid are described e.g. in U.S. Pat. No. 3 982 543. Homo and copolymers of lactic acid are described in e.g. U.S. Pat. No. 3 636 956. Examples of commercially available materials are Vicryl® (a copolymer of 90% glycolic acid sold by Ethicon, Sommerville, N.Y., U.S.A.—also known as Polyglactin) and Dexon® (Davies & Geck, Pearl River, N.Y., U.S.A.). Further examples are polydesoxazon (PDS) (Ethicon, U.S.A.), polyhydroxybutyric acid (PHB), copolymers of hydroxybutyric acid and hydroxyvaleric acid (PHBV), polyesters of succinic acid, and crosslinked hyaluronic acid. As suggested above, mixtures of the above-mentioned materials may equally well be employed. One skilled in the art would have no difficulty to modify such bioresorbable materials depending on current needs, e.g. with regard to resorption time, strength etc.

Possibly, growth factors may be included in the porous structure, either deposited in the pores or included in the bioresorbable material for slow release of growth factor.

The sheet-formed material according to the invention may suitably, in particular in application for strong muscles and in other locations where the material is subject to strong load, be combined with a resorbable armament e.g. a woven or knitted cloth.

The invention is further described with reference to the following examples.

Example 1

Preparation of a sheet material for replacement of a part of the pericardium.

5 ml of a solution of 10 g Biopol (PHBV, 20% hydroxyvaleric acid) in 100 ml dimethylacetamide (about 50° C.) was spread on a glass plate. The glass plate was thereafter placed in water of ambient temperature for 12 hours. In this manner a porous patch (8×8 cm) was formed having about 1 mm thickness. The patch was washed in water, dried, packed and sterilized (ethylene oxide).

Example 2

Use for healing of pericardiac defects.

In connection with cardiac surgery, difficulties occur almost always in closing the pericardium. This results in the pericardium often being left open. The result is adhesion which causes severe difficulties on re-operations and also an decreased motility of the heart, the function of which is impaired.

In connection with cardiac operations on sheep the defect caused was replaced with a patch of tissue-compatible resorbable polymer prepared according to Example 1. The patch was stitched into the defect by a continuous suture. When the animal after four months of healing was sacrificed and autopsy was performed, virtually normal pericardiac tissue was found to be formed without growing together with the heart surface, and the heart had been freely motile in the pericardium.

Example 3

Producing a nonwoven patch for reconstruction of pericardium.

The nonwoven material was made from solution spun PHB-fibres pressed together to a patch (produced in accordance with U.S. Pat. No. 4,603,070). Patch thickness was about 0.4 mm with about 70 per cent pore volume, patch size 15×15 cm. The patch was sterilized in ethylene oxide.

Example 4

Nonwoven PHB patches, produced according to Example 3, was used to replace a part of the pericardium in 10 sheep. The animals have been followed up for more than one year after the operation and have been sacrificed at different times. After two months regeneration of the pericardium had started, a very loose adhesion could be found. In the tissue a very active phagocytosis, with macrophages as the dominating type of cells, could be seen. No other kind of inflammation was present.

Later there were no signs of adhesion and already after four months a healing, very much like normal pericardium could be seen. The inner side was very smooth and glossy and mesothelial cells were present, which means that real pericardium had regenerated.

Up to ten months a slight darkness of the patch area could be observed due to partly remaining polymer. The darkness disappeared when all polymer was resorbed.

Example 5

Producing a tube for urethra reconstruction.

Vicryl®-fibre was knitted to form a thin tube. The tube mesh, 10 cm long, was mounted on a glass stick, diameter 4 mm. The tube was dipped in a solution of 10 g PHB:HV (80:20) in 100 ml DMAc and then dipped in water for 12 hours to get a porous structure. After washing, drying and packaging the urethra tube was sterilized in ethylene oxide.

Example 6

The urethra in 4 dogs was replaced by a urethra tube, produced according to Example 5. Six to nine months later the prosthesis had been resorbed and a fully functional urethra tissue was reconstructed in all animals.

We claim:

1. A material useful in the healing process of injured soft tissue and for the separation of injured soft tissue from other tissue in mammals, which comprises a porous flexible sheet or tube of a protein-free bioresorbable polymer about 10 μm–1 mm in thickness having a pore size of about 0.1 to 30 μm, which permits the passage of water and salts through the sheet or tube while restricting the passage of cells and other tissue particles; the polymer further consisting essentially of polyhydroxybutyric acid, a copolymer of hydroxybutyric acid and hydroxyvaleric acid or a combination of polyhydroxybutyric acid and a copolymer of hydroxybutyric acid and hydroxyvaleric acid.

2. A material according to claim 1, wherein the pore size is about 0.1–10 μm.

3. A method of separating injured soft tissue from surrounding tissue during the healing process so as to prevent undersired cells, tissue and foreign particles from coming into contact with the injured soft tissue, and to stimulate the formation of macrophages on the injured tissue, comprising separating the injured tissue from the surrounding tissue with a porous flexible sheet or tube comprising a protein-free bioresorbable polymer, the sheet or tube having a thickness of about 10 μm to 1 mm and having a pore size of about 0.1 μm to 30 μm so as to permit the passage of water and salt as well as peptides and precursors through the flexible sheet or tube while restricting the passage of cells, other tissue and foreign particles; the polymer further consisting essentially of polyhydroxybutyric acid, a copolymer of hydroxybutyric acid and hydroxyvaleric acid or a combination of polyhydroxybutyric acid and a copolymer of hydroxybutyric acid and hydroxyvaleric acid.

4. A bioresorbable support matrix for the replacement of soft tissue in mammals comprising a porous flexible sheet or tube of a protein-free bioresorbable polymer consisting essentially of polyhydroxybutyric acid, a copolymer of hydroxybutyric acid and hydroxyvaleric acid or a combination of polyhydroxybutyric acid and a copolymer of hydroxybutyric acid and hydroxyvaleric acid; the sheet or tube having a thickness of about 10 μm to 1 mm and having a pore size of about 0.1 μm to 30 μm.

5. A method of regenerating soft tissue in mammals which comprises placing a porous flexible sheet or tube comprising a protein-free bioresorbable polymer consisting essentially of polyhydroxybutyric acid, a copolymer of hydroxybutyric acid and hydroxyvaleric acid or a combination of polyhydroxybutyric acid and a copolymer of hydroxybutyric acid and hydroxyvaleric acid; the sheet or tube having a thickness of about 10 μm–1 mm and having a pore size of about 0.1 μm to 30 μm, in the area where the soft tissue is to be replaced and fastening the porous flexible sheet or tube to the adjoining or adjacent soft tissue, the sheet or tube serving as a support matrix for the growth of replacement tissue which sheet or tube is continually resorbed so as to be totally resorbed when the growth of replacement tissue is completed.

6. The method of claim 5 wherein the porous flexible sheet or tube is fastened to the adjoining or adjacent soft tissue by a continuous suture.

7. The method of claim 3 or 5 wherein the soft tissue is vascular/circulatory tissue.

8. The method of claim 3 or 5 wherein the soft tissue is urinary tissue.

9. The method of claim 3 or 5 wherein the soft tissue is muscle tissue.

10. The method of claim 3 or 5 wherein the soft tissue is a part of the pericardium.

11. The method of claim 3 or 5 wherein the sheet or tube has a pore size of about 0.1 μm–10 μm.

12. A method for stimulating the regeneration and healing of injured soft tissue in mammals wherein said injured tissue is separated from surrounding tissue with a porous flexible sheet or tube of a protein-free bioresorbable polymer, which polymer simultaneously excludes cells and other tissue particles detrimental to the healing process while also stimulating the formation of macrophages at the injured area and wherein the polymer has a thickness of about 10 μm to 1 mm and a pore size of about 0.1 μm to 30 μm and consists essentially of polyhydroxybutyric acid, a copolymer of hydroxybutyric acid and hydroxyvaleric acid or a combination of polyhydroxybutyric acid and a copolymer of hydroxybutyric acid and hydroxyvaleric acid.

13. The method of claim 12, wherein the sheet or tube has a pore size of about 0.1 μm to 10 μm.

14. The method of claim 12, wherein the soft tissue is a part of the pericardium.

15. The method of claim 12, wherein the soft tissue is vascular/circulatory tissue.

16. The method of claim 12, wherein the soft tissue is urinary tissue.

17. The method of claim 12, wherein the soft tissue is muscle tissue.

18. The method of claim 12, wherein the soft tissue is digestive tissue.

19. The method of claim 12, wherein the soft tissue is reproductive tissue.

20. The method of claim 12, wherein the soft tissue is respiratory tissue.

* * * * *